United States Patent [19]
Shekalim

[11] Patent Number: 5,689,850
[45] Date of Patent: Nov. 25, 1997

[54] ACCESSORY DEVICE FOR TOOTHBRUSHES

[75] Inventor: Avraham Shekalim, Nesher, Israel

[73] Assignee: Eureka Technologies Innovation Engineering (1987) Ltd., Migdal, Israel

[21] Appl. No.: 579,099

[22] Filed: Dec. 27, 1995

[30] Foreign Application Priority Data

Dec. 30, 1994 [IL] Israel .................................. 112207

[51] Int. Cl.$^6$ .................................. A46B 17/00
[52] U.S. Cl. .................. 15/22.1; 15/145; 15/176.6
[58] Field of Search .................. 15/22.1, 22.2, 15/22.4, 176.1, 176.6, 145; 279/23.1

[56] References Cited

U.S. PATENT DOCUMENTS

| | | | |
|---|---|---|---|
| 2,095,956 | 10/1937 | Bess . | |
| 2,875,458 | 3/1959 | Tsuda | 15/22.1 |
| 3,142,852 | 8/1964 | Phaneuf et al. | 15/22.1 |
| 3,156,936 | 11/1964 | Hartman et al. | 15/22.1 |
| 3,168,834 | 2/1965 | Smithson | 15/22.1 |
| 3,196,299 | 7/1965 | Kott | 15/22.1 |
| 3,316,576 | 5/1967 | Urbush | 15/22.1 |
| 3,394,277 | 7/1968 | Satkunas et al. | 15/22.1 |
| 3,535,726 | 10/1970 | Sawyer | 15/22.1 |
| 3,562,566 | 2/1971 | Kircher | 15/22.1 |
| 4,192,035 | 3/1980 | Kuris | 15/22.1 |
| 4,458,374 | 7/1984 | Hukuba | 15/22 R |
| 5,283,921 | 2/1994 | Ng | 15/22.1 |

*Primary Examiner*—Tony G. Soohoo
*Attorney, Agent, or Firm*—Ladas & Parry

[57] ABSTRACT

An accessory device for use with a conventional toothbrush having a handle at one end and bristles at the opposite end, includes a housing of a size and configuration to be grippable by a user's hand, a holder pivotally mounted within the housing and removably receiving the handle of a conventional toothbrush with the bristles of the toothbrush projecting externally of the housing, and a drive coupled to the holder for cyclically pivotting the holder and the toothbrush held thereby.

12 Claims, 1 Drawing Sheet

ACCESSORY DEVICE FOR TOOTHBRUSHES

FIELD AND BACKGROUND OF THE INVENTION

The present invention relates to toothbrushes, and particularly to an accessory device for use with conventional toothbrushes to enhance the effectiveness of the toothbrush for cleaning teeth.

It is now generally recognized that the cleaning action of toothbrushes can be enhanced by driving the toothbrush through cyclical motions over the surfaces of the teeth to be cleaned. A large number of electrically-driven toothbrushes have been developed for this purpose. The known electrically-driven toothbrushes, however, generally utilize a toothbrush of special construction usually supplied with the electrical drive. This forces the user to use the toothbrushes supplied by the supplier of the electrical drive, which not only increases the cost of the toothbrushes, but also deprives the user of the possibility of making a personal selection of the toothbrush from the large number of toothbrushes commercially available.

Since toothbrushes should be replaced at frequent intervals, these drawbacks in the existing electrically-driven toothbrushes frequently result in the toothbrush not being replaced at the proper times for best dental hygiene.

OBJECTS AND BRIEF SUMMARY OF THE INVENTION

An object of the present invention is to provide an accessory device which may be used with conventional hand-held toothbrushes and which, therefore, does not have the above drawbacks of the existing electrically-driven toothbrushes.

According to one aspect of the present invention, there is provided an accessory device for use with a toothbrush having a handle at one end and bristles at the opposite end. The device comprises a housing grippable by a user's hand; a holder pivotally mounted within the housing and having a longitudinal axis parallel to the longitudinal axis of the housing, the holder having an open end for removably receiving the handle of a toothbrush with the bristles of the toothbrush projecting externally of the housing; and a leaf spring secured at one end to the holder adjacent to the open end of the holder and extending within the holder parallel to the longitudinal axis of the holder. The leaf spring is formed with a deformable projection extending inwardly of the holder and engageable with the handle of a toothbrush when inserted into the open end of the holder, the opposite end of the leaf spring being unsecured so as to slidably engage the inner surface of the holder. A drive carried by the housing is coupled to the holder for cyclically pivotting the holder and the toothbrush held thereby.

According to another aspect of the present invention, there is provided an accessory device for the foregoing application comprising a housing grippable by a user's hand; a holder pivotally mounted within the housing and having a longitudinal axis parallel to the longitudinal axis of the housing, the holder having an open end for removably receiving the handle of a hand-held toothbrush with the bristles of the toothbrush projecting externally of the housing, the holder including a retainer member for releasably gripping the toothbrush handle when inserted through the open end of the holder; and a drive carried by the housing and coupled to the holder for cyclically pivotting the holder and the toothbrush held thereby, the drive including an electric rotary motor within the housing, and an eccentric coupling which couples the rotary motor to the holder. The housing includes a partition wall extending longitudinally within the housing parallel to the longitudinal axis of the housing and dividing its interior into a battery compartment for receiving an electrical battery to power the motor, and a second compartment for the toothbrush holder, electric motor and eccentric coupling.

According to still further features in the described preferred embodiment, the pivotal mounting is in the form of a ring of elastomeric material between the open end of the holder and an inner surface of the housing, permitting the holder and the toothbrush held thereby to pivot about two orthogonal axes, while at the same time sealing the interior of the housing.

As will be described more particularly below, an accessory device constructed in accordance with the foregoing features is adapted for use with conventional hand-held toothbrushes, and thereby enables the user to personally select almost any one of the wide variety of available toothbrushes according to the particular preference of the user. Moreover, since a much larger variety of toothbrushes are available for use in the accessory device, the net effect would be to reduce the overall cost to the user particularly because of the frequent replacements that should be made for best dental hygiene.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
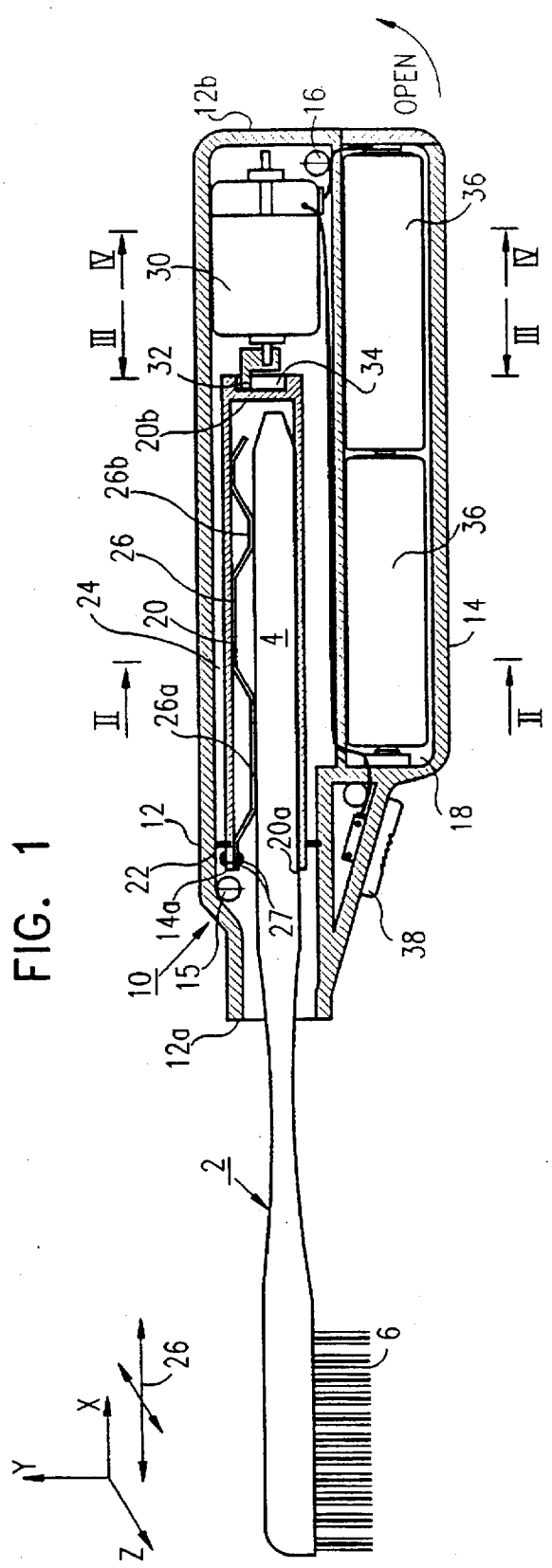
FIG. 1 is a longitudinal sectional view illustrating one form of toothbrush accessory device constructed in accordance with the present invention.
Figure 4:
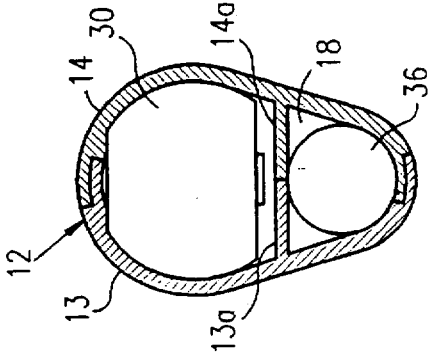
FIGS. 2, 3, and 4 are transverse sectional views, along lines II—II, III—III and IV—IV, respectively, of FIG. 1.
Figure 3:
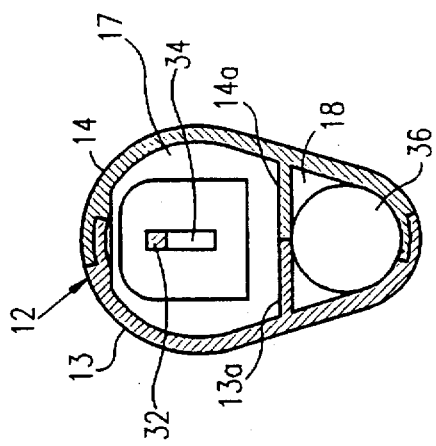
Figure 2:
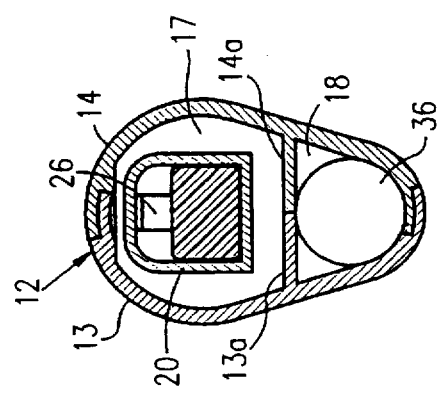

The accessory device illustrated in the drawings is adapted for use with a conventional hand-held toothbrush, generally designated 2, having a handle 4 at one end, and bristles 6 at the opposite end.

The accessory device, generally designated 10, includes a housing 12 of a size and configuration to be grippable by a user's hand. Housing 12 is open at one end 12a for receiving the handle 4 of the toothbrush 2, and is closed at its opposite end 12b. Preferably, the housing is made of two half-sections 13, 14, secured together by screws passing through bores 15, 16, at the opposite ends of the housing. Each half-section 13, 14 is formed with an internal half-partition 13a, 14a which, when the two housing sections are secured together, define a continuous partition extending parallel to the longitudinal axis of the housing, dividing the interior of the housing into an upper compartment 17 and a lower compartment 18.

A toothbrush holder, generally designated 20, is located within the upper housing compartment 17 and has a longitudinal axis extending parallel to the longitudinal axis of the housing. Holder 20 is open at one end 20a, adjacent to the open end 12a of housing 12, so that it may receive handle 4 of a conventional toothbrush 2, with the bristles 6 of the toothbrush projecting externally of the housing. The opposite end of holder 20 is closed by an end wall 20b.

Holder 20 is pivotally mounted within housing 12 by an elastomeric ring 22 received over the open end 20a of the holder and engageable with the inner surface of the housing 12. Elastomeric ring 22 spaces the outer surface of the holder from the inner surface of the housing by an annular space 24, thereby permitting the holder, and the toothbrush 2 held thereby, to pivot within the housing about two orthogonal axes, perpendicular to the longitudinal axis of the housing, namely about the Y-axis and the Z-axis as shown by the arrows 26 in FIG. 1.

Holder 20 includes a leaf spring 26 extending axially of the holder engageable with the toothbrush handle 4 for releasably retaining the toothbrush handle within the holder. Leaf spring 26 is fixed at one end by a fastener 27 to the open end of holder 20 and is formed with two projections 26a, 26b extending inwardly of the holder and engageable with the toothbrush handle 4 when inserted into the holder. Inwardly-extending projection 26a adjacent to the open end 20a of the holder is of longer axial length than projection 26b at the opposite end of the leaf spring. The opposite end of the leaf spring is unsecured so that it may slide along the inner surface of holder 20 when the two projections 26a, 26b are deformed by the engagement with the toothbrush handle 4.

Holder 20, and the toothbrush 2 inserted therein, are cyclically pivotted about elastomeric ring 22 by a drive including a rotary motor 30 connected to holder 20 by an eccentric coupling connected to the closed end wall 20b of the holder. The latter coupling includes a pin 32 rotated eccentrically by motor 30 and received within a transverse slot 34 formed in end wall 20b of holder 20, such that the rotation of eccentric pin 32 by motor 30 pivots the holder, and the toothbrush held thereby, about both the X-axis and the Z-axis as shown by the arrows 26 in FIG. 1.

Motor 30 is powered by two batteries 36 located in the battery compartment 18 of housing 12. The motor is energized by a manual switch 38 located adjacent to the open end 12a of the housing so as to be conveniently accessible to the user's index finger or thumb when gripping the housing.

The manner of using the illustrated device will be apparent from the above description.

Thus, the user may use the device with any conventional hand-held toothbrush by merely inserting the toothbrush handle 4 via the open end 12a of the housing 12 into the holder 20, and moving the toothbrush handle to the end of the holder, as shown in FIG. 1. This insertion of the toothbrush into the holder deforms the leaf spring 26 such that the spring releasably retains the toothbrush within the holder. When manual switch 38 is turned on to energize motor 30 by the batteries 36, the output shaft of motor 30 rotates eccentric pin 32 received in slot 34 in the end wall 20b of housing 20 such as to pivot the housing about the elastomeric ring 22. This causes the holder 20, and also the toothbrush 2 received therein, to cyclically pivot about both the X-axis and the Z-axis as shown by the arrows 26 in FIG. 1.

It will be appreciated that the elastomeric ring 22 not only permits these pivotal movements of the holder and the toothbrush held therein, but also seals the open end 12a of the housing and the interior of the holder 20, from the remaining interior of the housing, particularly from motor 30 and the batteries 36. Thus, any water entering holder 20 from the toothbrush is blocked by the elastomeric ring 24 from reaching motor 30 or the batteries 36.

Toothbrush 2 may be conveniently removed, or replaced by another conventional toothbrush whenever desired, by merely withdrawing the toothbrush from holder 20.

The illustrated device thus enables the user to use a conventional hand-held toothbrush with the device and to replace the toothbrush by another one whenever desired. Moreover, it enables the same device to be used by different users, e.g., many members of the family, each inserting his or her own toothbrush into the holder 20 and removing the toothbrush after use.

While the invention has been described with respect to one preferred embodiment, it will be appreciated that this is set forth merely for purposes of example, and that many other variations, modifications and applications of the invention may be made.

I claim:

1. An accessory device for use with a toothbrush having a handle at one end and bristles at the opposite end, said device comprising:

a housing grippable by a user's hand and having a longitudinal axis;

a holder mounted by a pivotal mounting within the housing and having a longitudinal axis parallel to the longitudinal axis of the housing, said holder having an open end for removably receiving the handle of a toothbrush with the bristles of the toothbrush projecting externally of the housing;

a leaf spring secured at one end to the holder adjacent to the open end of the holder and extending within the holder parallel to the longitudinal axis of the holder, said leaf spring being formed with a deformable projection extending inwardly of the holder and engageable with the handle of a toothbrush when inserted into the open end of the holder, the opposite end of the leaf spring being unsecured so as to slidably engage the inner surface of the holder;

and a drive carried by said housing and coupled to said holder for cyclically pivotting said holder and the toothbrush held thereby.

2. The device according to claim 1, wherein said one end of the leaf spring is secured to the holder by a fastener passing through the leaf spring and the holder adjacent to the open end of the holder.

3. The device according to claim 2, wherein said inwardly extending projection of the leaf spring is adjacent to the open end of the holder and is of relatively long axial length, said leaf spring being formed with a second inwardly extending projection adjacent to said opposite end of the leaf spring and of shorter axial length than said first-mentioned projection.

4. The device according to claim 1, wherein said drive includes a rotary motor within the housing, and an eccentric coupling which couples the rotary motor to the holder.

5. The device according to claim 4, wherein said pivotal mounting of the holder is in the form of a ring of elastomeric material between the open end of the holder and an inner surface of the housing, permitting the holder and the toothbrush held thereby to pivot about two orthogonal axes perpendicular to said longitudinal axis of the housing, while at the same time sealing the interior of the housing.

6. The device according to claim 5, wherein the end of the holder opposite to its open end is closed by an end wall, said eccentric coupling comprising a pin rotated eccentrically by said motor and received within a slot formed in said end wall of the holder.

7. The device according to claim 4, wherein said housing further includes a battery compartment for receiving electrical batteries to power said motor.

8. The device according to claim 7, wherein said housing further includes a partition wall extending longitudinally within the housing parallel to the longitudinal axis of the housing and dividing its interior into said battery compartment, and a second compartment for said holder, electric motor and eccentric coupling.

9. An accessory device for use with a toothbrush having a handle at one end and bristles at the opposite end, said device comprising:

a housing grippable by a user's hand and having a longitudinal axis;

a holder mounted by a pivotal mounting within the housing and having a longitudinal axis parallel to the longitudinal axis of the housing, said holder having an open end for removably receiving a handle of a hand-held toothbrush with the the bristles of the toothbrush projecting externally of the housing, said holder including a retainer member for releasably gripping the toothbrush handle when inserted through the open end of the holder; and a drive carried by said housing and coupled to said holder for cyclically pivoting said holder and the toothbrush held thereby, said drive including an electric rotary motor within the housing, and an eccentric coupling which couples the rotary motor to the holder;

said housing including a partition wall extending longitudinally within the housing parallel to the longitudinal axis of the housing and dividing its interior into a battery compartment for receiving an electrical battery to power said motor, and a second compartment for said holder, electric motor and eccentric coupling, wherein said retainer member is a leaf spring secured at one end to the holder adjacent to its open end and extending within the holder parallel to its longitudinal axis, said leaf spring being formed with a deformable projection extending inwardly of the holder and engageable with the handle of the toothbrush when inserted into the open end of the holder, wherein said one end of the leaf spring is secured to the holder by a fastener passing through the leaf spring and the holder adjacent to the open end of the holder, the opposite end of the leaf spring being unsecured and slidably engaging the inner surface of the holder.

10. The device according to claim 9, wherein said inwardly extending projection of the leaf spring is adjacent to the open end of the holder and is of relatively long axial length, said leaf spring being formed with a second inwardly extending projection adjacent to said opposite end of the leaf spring and of shorter axial length than said first-mentioned projection.

11. An accessory device for use with a toothbrush having a handle at one end and bristles at the opposite end, said device comprising:

a housing grippable by a user's hand and having a longitudinal axis;

a holder mounted by a pivotal mounting within the housing and having a longitudinal axis parallel to the longitudinal axis of the housing, said holder having an open end for removably receiving a handle of a hand-held toothbrush with the bristles of the toothbrush projecting externally of the housing, said holder including a retainer member for releasably gripping the toothbrush handle when inserted through the open end of the holder; and a drive carried by said housing and coupled to said holder for cyclically pivoting said holder and the toothbrush held thereby, said drive including an electric rotary motor within the housing, and an eccentric coupling which couples the rotary motor to the holder;

said housing including a partition wall extending longitudinally within the housing parallel to the longitudinal axis of the housing and dividing its interior into a battery compartment for receiving an electrical battery to power said motor, and a second compartment for said holder, electric motor and eccentric coupling, wherein said pivotal mounting of the holder is in the form of a ring of elastomeric material between the open end of the holder and an inner surface of the housing, permitting the holder and the toothbrush held thereby to pivot about two orthogonal axes perpendicular to said longitudinal axis of the housing, while at the same time sealing the interior of the housing.

12. The device according to claim 11, wherein the end of the holder opposite to its open end is closed by an end wall, said eccentric coupling comprising a pin rotated eccentrically by said motor and received within a slot formed in said end wall of the holder.

\* \* \* \* \*